United States Patent [19]

Patel

[11] Patent Number: 4,815,450

[45] Date of Patent: Mar. 28, 1989

[54] ENDOSCOPE HAVING VARIABLE FLEXIBILITY

[76] Inventor: Jayendra I. Patel, 502 Rector St., Valdese, N.C. 28690

[21] Appl. No.: 150,764

[22] Filed: Feb. 1, 1988

[51] Int. Cl.$^4$ .............................................. A61B 1/00
[52] U.S. Cl. ............................................ 128/6; 128/4
[58] Field of Search ........................... 128/3, 4, 5, 6, 7

[56] References Cited

U.S. PATENT DOCUMENTS

| | | | |
|---|---|---|---|
| 4,141,364 | 2/1979 | Schultze | 128/4 X |
| 4,148,307 | 4/1979 | Utsugi | 128/4 |
| 4,176,662 | 12/1979 | Frazer | 128/6 |
| 4,207,872 | 6/1980 | Meiri et al. | 128/4 |
| 4,577,621 | 3/1986 | Patel | 128/4 |
| 4,676,228 | 6/1987 | Krasner et al. | 128/4 |

*Primary Examiner*—William H. Grieb
*Attorney, Agent, or Firm*—Roy B. Moffitt

[57] ABSTRACT

An improved endoscope of the variety which includes an endoscope slideably nested inside of a guiding tube, including an improvement that renders on demand either the guiding tube more flexible than the endoscope or the endoscope more flexible than the guiding tube. The improvement may be one of several embodiments, namely: (a) channels in a thermosensitive guiding tube or endoscope for circulating warm or cold fluid therein; (b) a plurality of sphere-like bodies disposed in a chamber in the guiding tube or endoscope and a vacuum system adapted to remove air or a fluid medium from the chamber; (c) a pump connected to one or more channels in a guiding tube or endoscope for providing pressurized fluid in the channels; or, (d) a flexible covering connected to and surrounding at least a part of a guiding tube delimiting a space between the covering and the guide tube, the space being in communication with a means to supply fluid of a predetermined temperature and pressure to the space.

15 Claims, 4 Drawing Sheets

ENDOSCOPE HAVING VARIABLE FLEXIBILITY

RELATED PATENTS

This application relates to and is an improvement over the subject matter disclosed in U.S. Pat. No. 4,577,621.

BACKGROUND OF THE INVENTION

The prior art endoscope referred to above is composed of certain basic elements, namely a control unit, a first flexible tube having a free end connected to the control unit and an optical transmission system in the first flexible tube connected to the control unit for viewing outside images. Circumscribing a portion of the first flexible tube is a guide tube (second flexible tube) that is used in combination with a device circumscribing the terminal end portion of the first flexible tube (near the free end of the first flexible tube) to incrementally help advance the combination of endoscope and guide tube along a narrow passageway, such as a human colon. The incremental advance is achieved by first advancing the first flexible tube (endoscope) a short distance into the passageway sought to be penetrated and beyond the end of the guide tube, then the guide tube is advanced a predetermined distance over the first flexible tube. This procedure is repeated over and over until the location within the cavity sought to be penetrated is reached.

It has been found that there exists a relationship between the flexibility of the guiding tube and the flexibility of the first flexible tube (endoscope) relative to the ease of use of such apparatus. When the flexibility of the guiding tube and the endoscope are essentially the same, there are certain instances where the advancement of the endoscope beyond the guiding tube and then the advancement of the guiding tube over the endoscope creates problems either to the operator or to the patient. In operation, when the endoscope (first flexible tube) is advanced, the guiding tube is held stationary. It has been found that it is easier to advance the endoscope through the guiding tube if the guiding tube is stiffer than the endoscope, and it is easier to advance the guiding tube over the endoscope if the guiding tube was more flexible than the endoscope. It was further realized that the change in flexibility of stiff to flexible and from flexible to stiff of the guiding tube should be under the control of the person using it. Thus, the operator of the improved endoscope of the instant invention has control over the flexibility of the guiding tube or the endoscope relative to when it will become more flexible and when it will become less flexible.

To fully appreciate the understanding of the instant invention, the invention disclosed by U.S. Pat. No. 4,577,621 should be consulted. The means disclosed and claimed in this patent for advancing the free end of an endoscope along a narrow passageway, are shown in FIGS. 2, 3, 4(a), 4(b), 5, 6(a), 6(b), 7(a), 7(b), 8a, and 8(b) of this patent. Such means per se form no part of the novelty of the present invention, but may form a part in the overall combination as herein disclosed and claimed. Any such means are believed to be adequately described in the specification of U.S. Pat. No. 4,577,621, and such disclosure is incorporated herein by express reference.

BRIEF DESCRIPTION OF THE INVENTION

The invention is composed of five embodiments: One embodiment comprises the elements of a control unit, a first flexible tube having a first end portion connected to the control unit and the second end portion having a free end. The first flexible tube is an endoscope and it contains an optical means disposed in it communicating with the control unit and the free end for illuminating and viewing images outside of the endoscope. Also included is a second flexible tube (a guide tube) circumscribing at least a part of the endoscope. Either the guide tube or the endoscope, has a wall made from thermosensitive plastic. Such plastic is adapted to be rendered more flexible when brought into contact with a heated fluid medium (heated water for example) and less flexible when brought into contact with a cooled fluid medium (cooled water for example). The materials from which the guide tube and endoscope are made are selected so that the particular item (guide tube or endoscope) not made of thermosensitive material is less flexible than the other when the other is subjected to heated fluid medium. Also included is a pump and a heater/cooler for supplying fluid (such as water and the like) of a predetermined temperature (heated/cooled) to channels in the endoscope or the guide tube. There may be a means attached to the second flexible tube for facilitating the advancement of the free end of the guide tube along a narrow passageway, such means being those shown in U.S. Pat. No. 4,577,621. The use of such means is incidental and not necessary to the making and using of the invention.

Another embodiment employs the basic elements of the embodiment described above, however, either the plastic guide tube or the endoscope has a channel therein connected to a pressurized fluid-supplying device. This combination creates a guide tube or endoscope that can be rendered flexible and non-flexible by the use of fluid pressure alone. A piece of plastic having a channel therein and connected to a pressure fluid-supplying device can be rendered non-flexible on command by applying pressurized fluid to the channels (either a static or flowing condition) to build up pressure inside the channels and flexible by relieving such pressure. The pressure itself is enough to make the plastic of the guide tube or endoscope go rigid. This embodiment is not a preferred embodiment because use of high pressure inside a human cavity to create rigidity presents possible unwanted safety hazards.

Still another embodiment contains the same basic structure of the first-mentioned embodiment, except that neither the guide tube or endoscope walls are made from thermosensitive plastic. The guide tube or endoscope has a composite wall that delimits a passageway (a tube) in which is disposed the endoscope. The composite wall has a non-porous outer and inner wall spaced apart from each other delimiting a space between them. In this space are a plurality of sphere-shaped bodies in a fluid (gas or liquid) medium. At least one channel is disposed in either the non-porous or outer or inner wall, which is in communication with this space. Instead of a pressure pump to create pressure in the channel, there is a vacuum pump in communication with a channel in the non-porous outer/inner wall for removing fluid from the space to create a partial vacuum therein. The vacuum causes the guide tube wall to become non-flexible in a given configuration and removal of the vacuum plus the co-action of the spheres causes the wall of the guide tube to become flexible.

Like the third mentioned embodiment, another embodiment also has a composite wall delimiting a passageway (a tube) in which is disposed the endoscope. This composite wall comprises the wall of the endoscope or guide tube and is composed of a non-porous outer wall and a non-porous inner wall spaced apart from the non-porous outer wall, plus a porous member disposed in between the non-porous outer and inner wall. This porous member delimits first and second spaces between the outer and inner wall and disposed in one of such spaces is a plurality of sphere-shaped solid bodies of a size larger than the pores of the porous member in a fluid medium. A channel exists in the non-porous wall connecting a vacuum pump to the space occupied by the spheres and is adapted to remove the fluid medium from the space not otherwise occupied by the spheres in order to render the composite wall rigid on command. Releasing the vacuum causes the composite wall to become flexible.

Another embodiment employs the basic elements of the first mentioned embodiment except that only the guide tube need be constructed of thermosensitive material and has, in addition thereto, a flexible covering circumscribing at least a part of the guide tube and delimiting a space between the covering and the guide tube. The space is in communication with channels in the wall of the guide tube and the channels communicate with a device for supplying and withdrawing fluid of a predetermined temperature and pressure to the space so that the flexible covering may be expanded and contracted and the guide tube heated and cooled on demand.

DETAILED DESCRIPTION OF THE INVENTION

Figure 2:
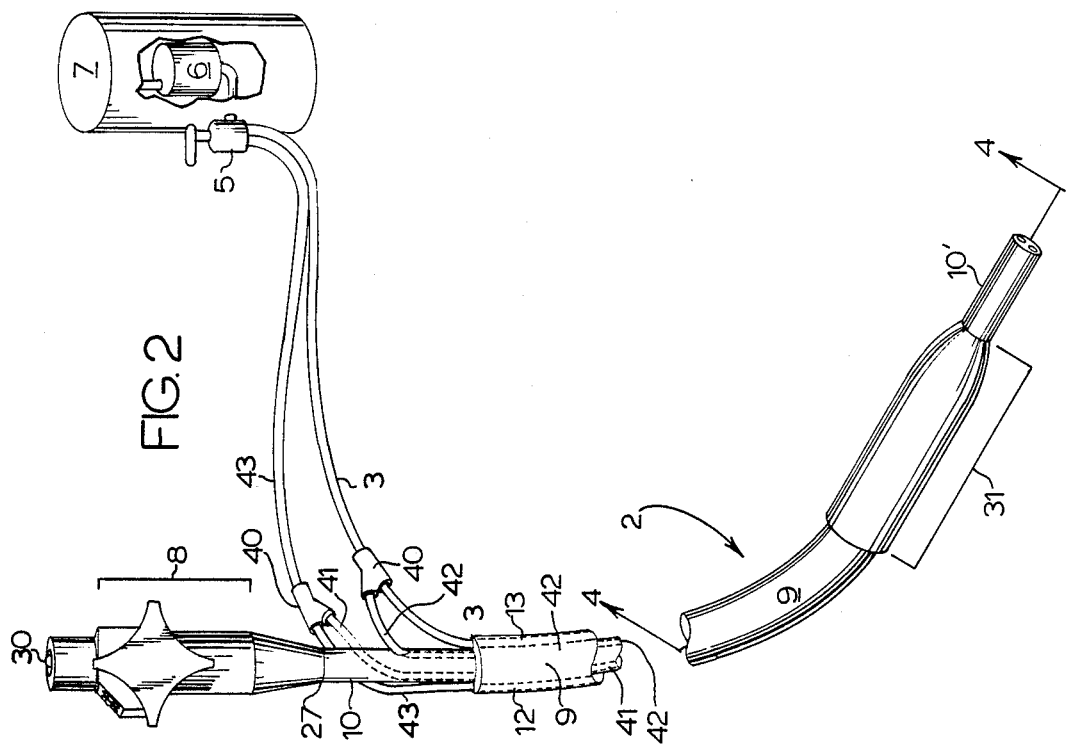
FIG. 2 is a perspective view of one embodiment of the present invention employing a fluid to effect the flexibility of a guide tube and/or the endoscope of the prior art endoscope of FIG. 1.
Figure 1:
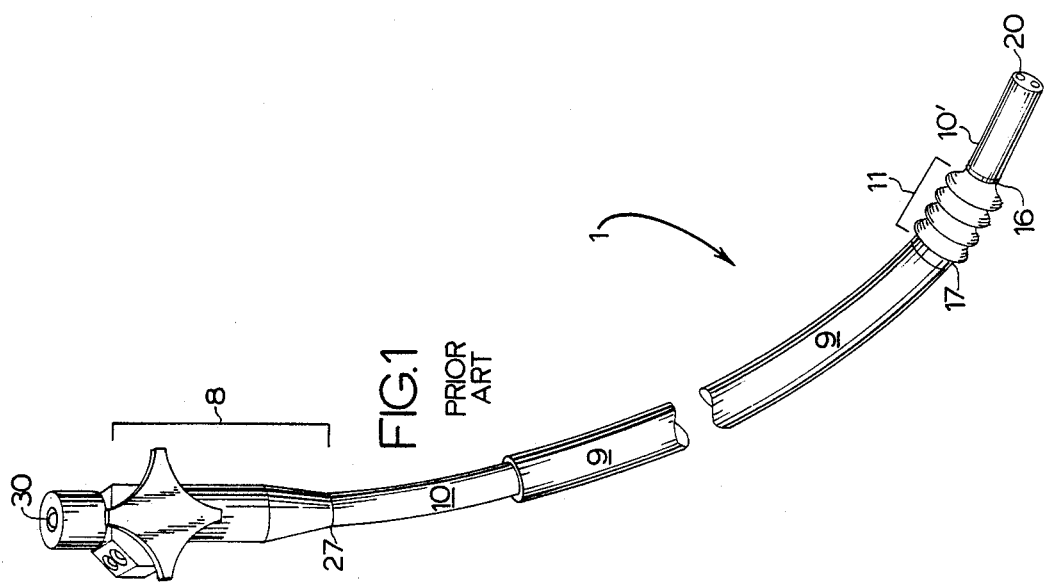
FIG. 1 is a perspective view of the prior art a endoscope.

U.S. Pat. No. 4,577,621 has been referred to previously and its contents have been expressly incorporated herein by reference. FIGS. 1 and 2 of this specification contains some features common to those shown in FIGS. 2 and 3 of the aforementioned patent. More specifically, FIG. 1 of this specification is a duplication of the prior art as shown in FIG. 2 of U.S. Pat. No. 4,577,621. Element 1 is the prior art endoscope, such endoscope having a view device 30 attached to a control 8. Proximate end 27 is attached to the control and guide tube 10, which terminates in a distal portion 10'. Distal portion 10' also has a free surface on which there is exposed optical elements 20, such optical elements being contained in element 10 and in communication with control 8 and view device 30. Elements 20 are used to view images inside of a human organ such as a colon in the manner described in U.S. Pat. No. 4,577,621 and the prior art referred to in such patent. The endoscope of element 1 also has a guide tube 9 circumscribing a portion of endoscope 10. Guide tube 9 has a a bellows or accordion-like device 11 attached to element 9 at 17 and to element 10' at 16. The operation of the endoscope of element 1 is adequately described in U.S. Pat. No. 4,577,621, more particularly FIGS. 9a, 9b, and 9c of this patent, and reference is made thereto for further details.

Comparing FIGS. 1 and 2, certain differences will be noted among which will be element 31. Element 31 is a device that accomplishes the same purpose as element 11 and is an equivalent thereto. Its structure and operation is also adequately disclosed in U.S. Pat. No. 4,577,621 and reference is made thereto for further details, specifically, FIGS. 7a and 7b of such patent. Both element 11 and element 31 are devices that aid the advancement of the endoscope 1 or 2 along an organ like that of a human colon, but are not necessary to the making and using of the present invention and may be deleted. Endoscope 2 is made up of certain elements that are common to the prior art, namely view piece 30, control 8, and proximate end 27, endoscope 10, guide tube 9, distal end 10', and optical elements 20. Throughout this specification, elements 9 and 10 are referred to as guide tube and endoscope respectively, but they also may be referred to as first and second flexible tubes as well. They are flexible tubes, at least one being made from any convenient plastic such as polyvinyl chloride, except for those embodiments employing the spheres of FIGS. 5 and 6, as hereinafter more fully explained and rigidity caused by pressure.

Figure 4:
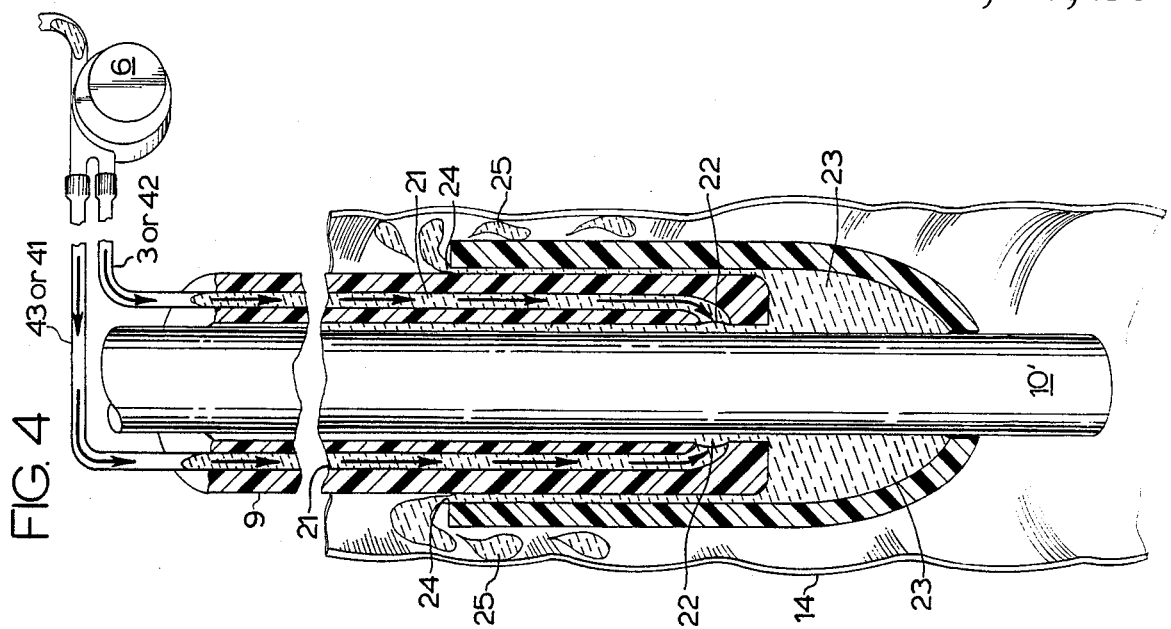
FIG. 4 is a cross-sectional view of another embodiment of the present invention, showing the particular embodiment in its intended environment, using a heated or cooled fluid to effect the flexibility of either the guide tube or the endoscope of FIGS. 2 and 3.

The obvious difference between element 1 and element 2 of FIGS. 1 and 2 respectively are channels 12 and 13 in guide tube 9 or endoscope 10, tubes 3 and 43, valve 5, pump 6, container 7 and valves 40. Channels 12 and 13 are connected to tubes 3 and 43 and valve 5. Valve 5 is connected to heat exchanger 7 in which there is a pump 6. Valve 5 is adapted to direct/permit the flow of fluid (water for example) down tube 43 and channel 12 or to stop such flow. Channel 12 may be deadended, as contemplated by FIG. 2, or it may be openended as shown by FIG. 4. In other words, viewing FIG. 4 and comparing it to FIG. 2, the embodiment of FIG. 2 does not have the ports as shown by elements 22. They would be sealed off and in such an embodiment, channel 21 corresponds to channels 12 and 13. Pressurized fluid is forced down tubes 3 and 43 into channels 13 and 12 respectively. The pressure of the fluid in channels 12 and 13 causes guide tube 9 to become rigid and less flexible than endoscope 10 or vice versa. Relief of such pressure obviously causes guide tube 9 or endoscope 10 to become more flexible. Thus, there is shown an apparatus, underneath the control of an operator, that can increase and decrease the flexibility of guide tube 9 or endoscope 10 upon command. Because the above described embodiment employs use of high pressure fluid to decrease the flexibility and increase rigidity, it is not the preferred embodiment of the embodiments disclosed in this specification. The presence of high pressure fluid in channels 12 and 13 while such are inside a human cavity, presents obvious safety concerns that may not be acceptable under certain circumstances.

Figure 3:
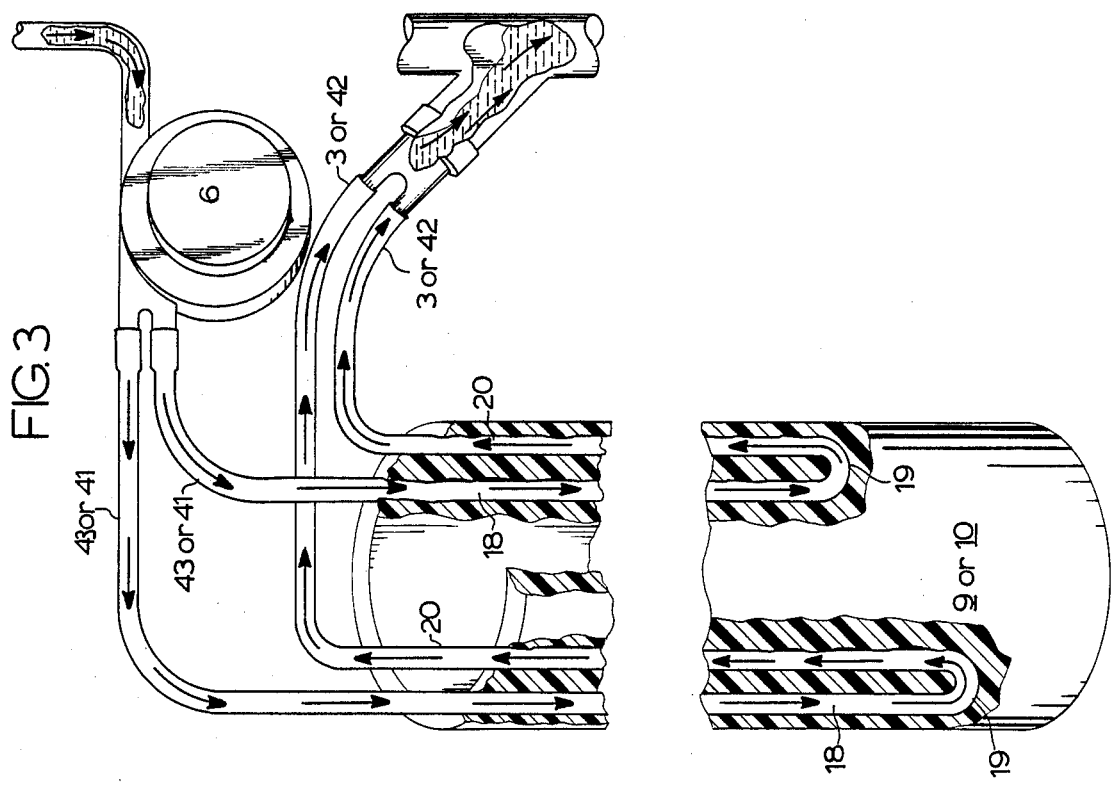
FIG. 3 is a cut-a-way view of a portion of the channels in either the guide tube or the endoscope and one embodiment of the fluid pumping system to effect the flexibility of either the guide tube or endoscope of FIG. 2.

Turning now to FIG. 3, there is shown a second embodiment and one of the preferred embodiments of the invention. FIG. 3 is to be viewed in conjunction with FIG. 2 and more particularly guide tube 9 and endoscope 10. In this embodiment, guide tube 9 and/or endoscope 10, is made of some thermosensitive material such as thermosensitive polyvinyl chloride and guide tube 9 or endoscope 10 has in it "U"-shaped channels having legs 18 and 20 and a "U" shaped portion 19. Tubes 43 are connected to channels 18 and tubes 3 are connected to channels 20. Following the flow arrows in tubes 3 and 43, 41 and 42, and channels 18 and 20, heated fluid (such as water) is pumped into guide tube 9 or endoscope 10 by tubes 43 or 41, into channel 18, around "U" shaped portion 19, and is discharged through channel 20 into tubes 3 or 40, back into a return to be reheated, or cooled as the case may be. The heat in the fluid causes the thermosensitive plastic comprising guide tube 9 or endoscope 10 to become more flexible than it would otherwise be at room temperature. By reversing the process, i.e., pumping cold fluid into tubes 43 or 41 and channels 18 and 20, the increased degree of flexibility of guide tube 9 or endoscope 10 achieved by using hot fluid is reversed. Two way valves 40 permit the fluid from 7 to flow in the endoscope 10 if it is the part of the improved endoscope that is made from the thermosensitive plastic sought to be rendered more flexible than the guide tube 9. Since both elements 9 and 10 could be made from thermosensitive plastic, only one is adapted to be rendered more flexible relative to the other on demand as shown. Furthermore, the requirement of thermosensitive plastic for elements 9 and/or 10 can be deleted and pressurized fluid, either in 9 or 10, used to rigidify same. Thus there is shown an apparatus that can cause guide tube 9 or endoscope 10 to become more flexible or less flexible on command by the use of hot and cold fluids relative. Endoscope 10 can be rendered more flexible than guide tube 9 on demand by the use of valves 40, and the reverse, 9 more flexible than 10, also by the use of valve 40.

Attention now is drawn to FIG. 4 wherein there is shown another preferred embodiment of the invention. In this embodiment, tube 41 or 43 is connected to channel 21, which has an opening 22 in its distal end. Warm or cooled fluid is pumped in through tubes 3, 43, 41, or 42, allowed to flow through channel 21 and out port 22 into cavity 23 and through that constriction formed by elements 9 and 31 shown by element 24 into cavity 25 which is that cavity formed by the organ 14 into which the endoscope has penetrated. Fluid 25 then is allowed to enter organ 4 and to flow out of the organ in the same manner as that organ expels fluid otherwise internally generated Warm or cooled fluid, such as water or other non-toxic liquids, flowing through the aforementioned tubes and channel 21 causes the thermosensitive plastic forming guide tube 9 to become more flexible than it otherwise would be at room temperature therein or rigid in the case of cooled fluid. By decreasing the temperature of fluid 25 in the tubes, the thermosensitive plastic of guide tube 9 becomes more rigid, all on command of the operator.

Guide tube 10 of FIG. 4 can be made from thermosensitive polyvinylchloride but not guide tube 9. In such a structure, the warm fluid 25 would render endoscope 10 more flexible than guide tube 9 and when fluid 25 was cooled, endoscope 10 would be rendered more rigid compared to the state of flexibility achieved by use of warm fluid.

Figure 5:
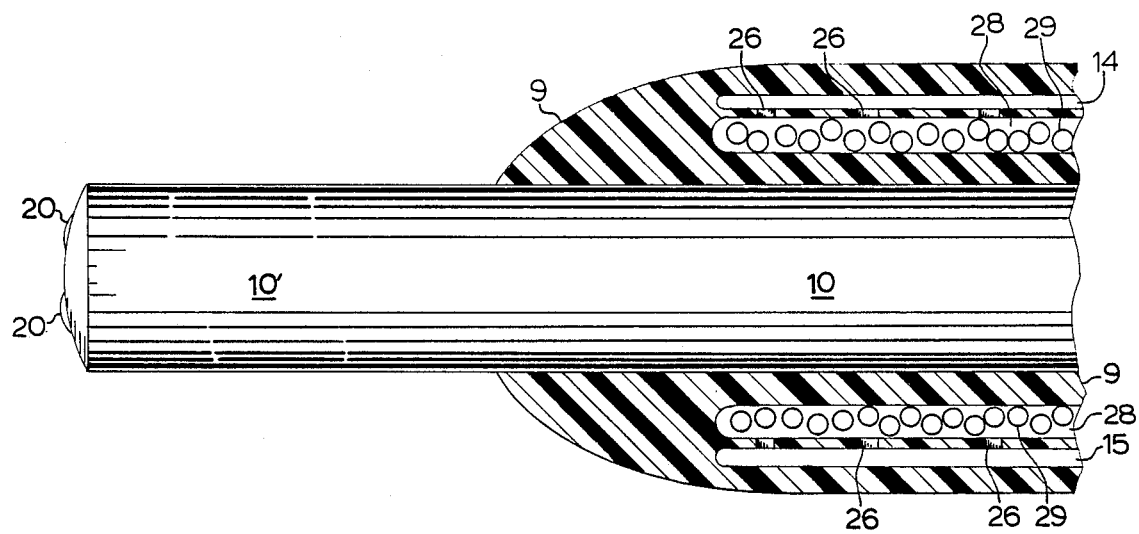
FIG. 5 is a cross-sectional view of still another embodiment of the present invention employing loosely-disposed spheres in a chamber within a guide tube to effect its flexibility.

Another preferred embodiment of the invention is shown in FIG. 5. This embodiment has a structure similar to that of previous embodiments except that guide tube 9 has chambers 28 and 14. It will be noted that chamber 14 communicates with chamber 28 through inlet/outlet port 26. Disposed in chamber 28 are a plurality of spheres (such as plastic spheres) in a fluid medium (air or liquid). Spheres 29 are loosely disposed and are movable within chamber 28. Channel 14 is in communication with a pump (not shown) such as a vacuum pump that can eliminate only fluid or air within chambers 14, ports 16, and chamber 28. When this happens, the flexibility o guide tube 9 is reduced and it becomes more rigid. When air or fluid pressure is restored, guide tube 9 becomes more flexible. This embodiment allows for an operator to control the flexibility of guide tube 9 and to change that flexibility on demand by merely evacuating air or fluid from chambers 14, 26, and 28 to rigidify guide tube 9 and to restore the air pressure to such chambers in order to make guide tube 9 more flexible. The wall of endoscope 10 could be likewise construed, i.e., like the composite wall of element 9, which would render its flexibility under the control of the operator like that described for element 9.

Figure 6:
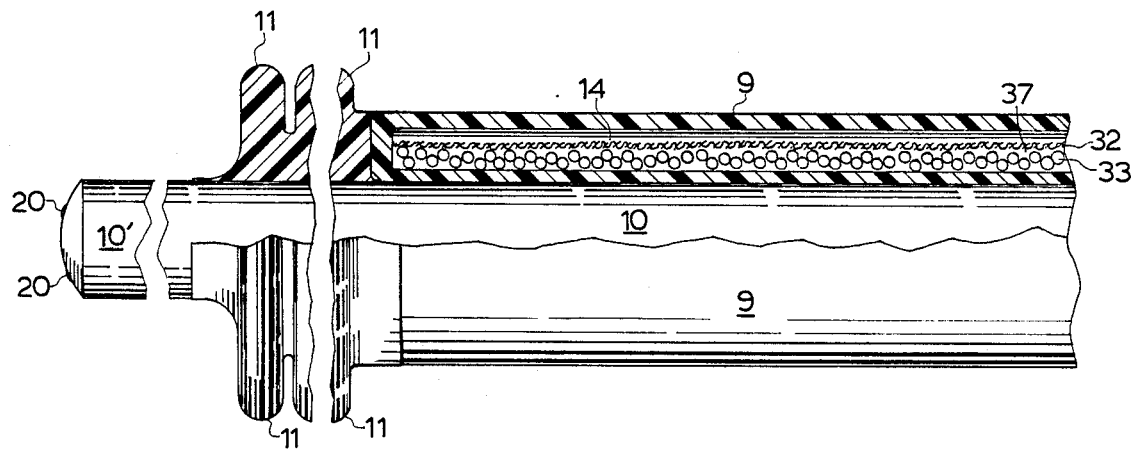
FIG. 6 is a cross-sectional view of a modification of the embodiment shown in FIG. 5.

FIG. 6 depicts another preferred embodiment of the invention and is a species of the embodiment shown in FIG. 5. In this particular embodiment accordion element 11 is shown rather than element 31, it being understood that throughout all embodiments of this invention, either element 31 or 11 can be used interchangeably and/or they may be all together deleted. The embodiment of FIG. 6 works in the same manner as the embodiment of FIG. 5. The sidewall of guide tube 9 (or endoscope 10) contains two chambers, namely 14 and 37. The two chambers are separated from the other by a porous member 32, such as nylon mesh. In chamber 37 there are loosely disposed a plurality of spheres 33, like that of spheres 29 of FIG. 5 in a fluid or gaseous medium. Chamber 14 is in communication with a vacuum pump, (like chamber 14 of FIG. 5) and upon removing air or fluid from chamber 14 and chamber 37, guide tube 9 (or endoscope 10) is rendered rigid compared to the flexible state of endoscope 10 (or guide tube 9). The wall of endoscope 10 can be constructed like that of the composite wall just previously described for element 9 thus rendering it adapted to be made rigid and non-rigid on demand in a likewise fashion. As it was with all previous embodiments, this embodiment is an improved endoscope whose guide tube or endoscope can be made flexible or non-flexible on demand by an operator by applying or not applying a vacuum through chambers 14 and 37.

Figure 7:
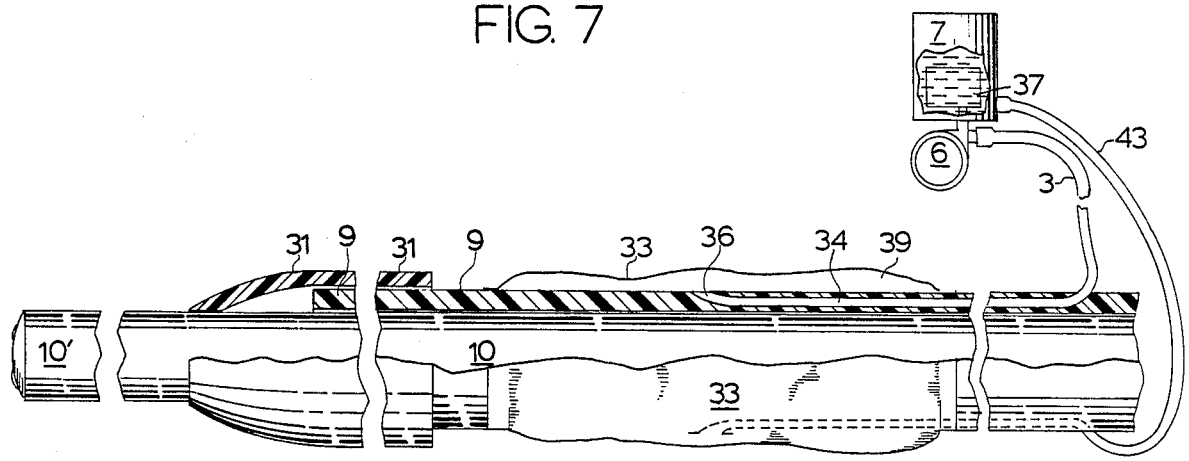
FIGS. 7 and 8 are cross-sectional views of still another embodiment of the present invention that employs an inflatable and deflatable member attached to the outside of a guide tube into which hot or cold fluid is pumped to effect the flexibility of the guide tube.
Figure 8:
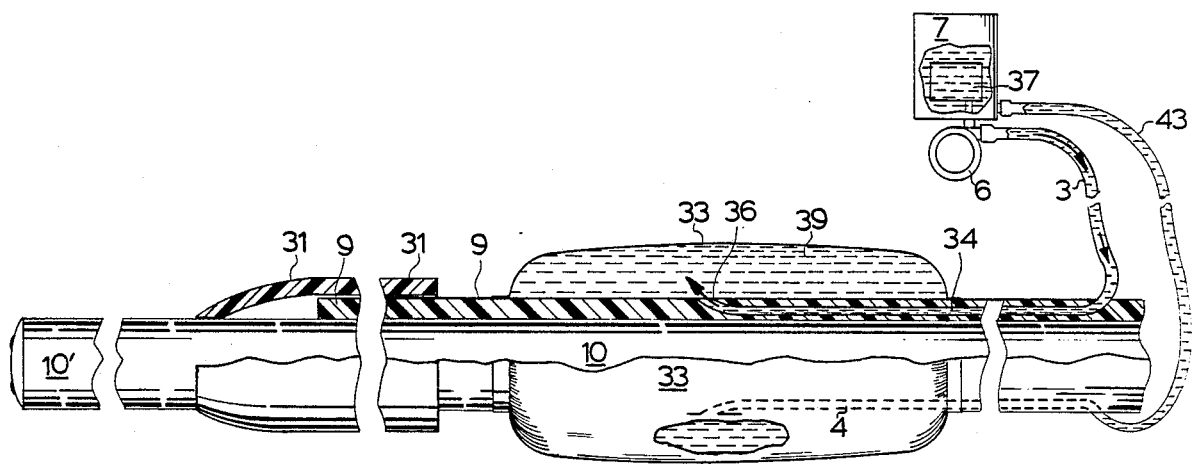

The last embodiment is also a preferred embodiment and is shown in FIGS. 7 and 8. This embodiment contains a flexible and inflatable sack 33 attached to the outside surface of guide tube 9 delimiting chamber 39. Inflatable sack 33 is attached to the outside surface of guide tube 9 in two places to form chamber 39. Chamber 39 is in communication with tubes 3 and 43 by means of port 36 and channel 34. Chamber 7, with heat exchanger 37 and pump 6, provides temperature controlled fluid (e.g., heated or cooled water) through either conduit 3 or 43 through chamber 34, port 36 into space 39 to inflate sack 33. The warm fluid causes guide tube 9 (made from thermosensitive plastic as above disclosed) to become more flexible on demand. Obviously, cold fluid can be pumped into either conduits 3 and 43 into sack 33 and chamber 39 to reverse the process and cause guide tube 9 to become more rigid than it otherwise would be with hot fluid in chamber 39. FIG. 7 shows this embodiment with sack 33 collapsed (no fluid therein) and FIG. 8 shows sack 33 fully extended with fluid (either hot or cold as the case may be) in chamber 39.

In the drawings and specifications, there have been set forth preferred embodiments of this invention and all those specific terms are employed in their generic and descriptive sense only and not for purposes of limitation.

In all cases it is to be understood that the above-described embodiments are illustrative of one of many possible specific embodiments which may represent the principles of my invention. Numerous and various other embodiments can be devised readily in accordance with these principles by those skilled in the art without departing from the spirit and scope of my invention.

What is claimed is:

1. An endoscope comprising:
   (a) a control unit;
   (b) a first flexible tube having a first end portion connected to the control unit and a second end portion having a free end;
   (c) an optical means disposed in said first flexible tube and communicating with said control unit and said free end for illuminating and viewing images outside of the first flexible tube;
   (d) a second flexible tube circumscribing the first flexible tube;
   (e) either the first or second flexible tube having a wall made from a material adapted to be rendered more flexible than the other flexible tube when brought into contact with a fluid; and,
   (f) a device in communication with either the first or the second flexible tube for supplying fluid of a predetermined temperature thereto.

2. The endoscope of claim 1 further including at least one passageway in the wall of either the first or second flexible tube through which a fluid may be disposed, said passageway in communication with said means for supplying fluid of a predetermined temperature.

3. The endoscope of claim 1 including a space delimited by the outermost surface of the first flexible tube and the innermost surface of the second flexible tube, said space in communication with said means for supplying fluid of a predetermined temperature.

4. The endoscope of claim 2 wherein said passageway is undulating and has two end members and said means for supplying fluid of a predetermined temperature is connected to said end members of said undulating passageway and is adapted to force fluid of a predetermined temperature through one of said end members and withdraw such fluid from the other.

5. The endoscope of claim 2 further including a space delimited by the outermost surface of the first flexible tube and the innermost surface of the second flexible tube, said space in communication with said passageway.

6. The endoscope of claims 2, 4, or 5, wherein the means for supplying fluid of a predetermined temperature and pressure contains a heat exchanger for cooling and warming the fluid.

7. The endoscope of claim 1, further containing a means disposed at the second end portion of the first flexible tube for advancement of the free end of the first flexible tube along a narrow passageway.

8. An endoscope comprising:
   (a) a control unit;
   (b) a first flexible tube having a first end portion connected to the control unit and a second end portion having a free end;
   (c) an optical means disposed in said first flexible tube and communicating with said control unit and said free end for viewing images outside of the first flexible tube;
   (d) a second flexible tube circumscribing the first flexible tube;
   (e) either the first or the second flexible tube having a composite wall, said composite wall comprising a non-porous outer wall and a non-porous inner wall spaced apart from each other and delimiting a space therebetween, a plurality of sphere-shaped bodies and a fluid disposed in said space, and at least one channel in said non-porous outer or non-porous inner wall in communication with said space; and,
   (f) a device in communication with the channel in said non-porous outer or inner wall for removing fluid from said space.

9. The endoscope of claim 8 further containing a means disposed at the second end portion of the first flexible tube for advancing the free end of the first flexible tube along a narrow passageway.

10. An endoscope comprising:
    (a) a control unit;
    (b) a first flexible tube having a first end portion connected to the control unit and a second end portion having a free end;
    (c) an optical means disposed in said first flexible tube and communicating with said control unit and said free end for viewing images outside of the first flexible tube;
    (d) a second flexible tube circumscribing the first flexible tube;
    (e) either the first or the second flexible tube having a composite wall, said composite wall comprising a non-porous outer wall, a non-porous inner wall spaced apart from said non-porous outer wall, an intermediate member containing holes therein disposed in between said non-porous inner wall and said non-porous outer wall delimiting first and second spaces therebetween and a plurality of bodies of a size larger than the holes of the intermediate member and a fluid disposed within said first space; and,
    (f) a device in said outer wall in communication with the second space for removing fluid through the porous member from said first space.

11. The endoscope of claim 1 wherein said means in communication with the second flexible tube for supplying fluid of a predetermined temperature to said second flexible tube for chainging its flexibility comprises a covering at least partially surrounding and connected to the outer surface of said second flexible tube delimiting a space between the covering and the second flexible tube, said space in communication with said means for supplying fluid of predetermined temperature and pressure.

12. The endoscope of claims 11 wherein said covering is flexible and adapted to be expanded by supplying fluid to the space and contracted by withdrawing fluid from the space.

13. The endoscope of claims 11 or 12 further including a channel in the second flexible tube, said channel in communication with the space delimited by and between the covering and the second flexible tube and the means for supplying a fluid of predetermined temperature.

14. The endoscope of claims 10, 11, or 12 further including a device disposed at the second end portion of the first flexible tube for advancing the free end of the first flexible tube along a narrow passageway.

15. The endoscope of claim 13 further including a device disposed at the second end portion of the first flexible tube for advancing the free end of the first flexible tube along a narrow passageway.

* * * * *